(12) United States Patent
Wickboldt et al.

(10) Patent No.: US 10,229,316 B2
(45) Date of Patent: Mar. 12, 2019

(54) COMPOUND COLLIMATING SYSTEM USING APERTURES AND COLLIMATORS

(71) Applicant: Synaptics Incorporated, San Jose, CA (US)

(72) Inventors: Paul Wickboldt, Walnut Creek, CA (US); Eric Jones, San Jose, CA (US)

(73) Assignee: Synaptics Incorporated, San Jose, CA (US)

( * ) Notice: Subject to any disclaimer, the term of this patent is extended or adjusted under 35 U.S.C. 154(b) by 161 days.

(21) Appl. No.: 15/199,856

(22) Filed: Jun. 30, 2016

(65) Prior Publication Data
US 2017/0220840 A1    Aug. 3, 2017

Related U.S. Application Data

(60) Provisional application No. 62/289,172, filed on Jan. 29, 2016.

(51) Int. Cl.
*G06K 9/00* (2006.01)
*G06F 3/041* (2006.01)
(Continued)

(52) U.S. Cl.
CPC .......... *G06K 9/0053* (2013.01); *A61B 5/0059* (2013.01); *A61B 5/1172* (2013.01);
(Continued)

(58) Field of Classification Search
CPC ............... G06K 9/0053; G06K 9/0008; G06K 9/00013; G06K 9/0004; G06K 2009/0006;
(Continued)

(56) References Cited

U.S. PATENT DOCUMENTS 5,726,443 A * 3/1998 Immega ................ G01S 17/026
250/208.1
6,856,383 B1   2/2005 Vachris et al.
(Continued)

FOREIGN PATENT DOCUMENTS

CN          102073860 A      5/2011
EP          0886958 B1       4/2001
(Continued)

OTHER PUBLICATIONS

International Search Report and Written Opinion issued in PCT/US2017/015107 dated Apr. 25, 2017.
(Continued)

*Primary Examiner* — Tony Ko
(74) *Attorney, Agent, or Firm* — Leydig, Voit & Mayer, Ltd.

(57) ABSTRACT

An optical sensor system having a compound aperture and collimator structure for collimating light includes: an input surface providing a sensing region for a biometric object; an aperture layer, disposed beneath the input surface; a plurality of light-blocking structures, disposed beneath the aperture layer, forming a plurality of collimators; and an image sensor, disposed beneath the plurality of light-blocking structures, wherein the image sensor is configured to detect light from the sensing region that has passed through the aperture layer and the plurality of collimators.

20 Claims, 8 Drawing Sheets

(51) Int. Cl.

| | |
|---|---|
| *G02B 27/30* | (2006.01) |
| *G02B 27/28* | (2006.01) |
| *A61B 5/1172* | (2016.01) |
| *H01L 27/32* | (2006.01) |
| *H04N 5/225* | (2006.01) |
| *A61B 5/00* | (2006.01) |
| *G02B 13/24* | (2006.01) |
| *G06F 3/042* | (2006.01) |
| *A61B 5/1455* | (2006.01) |
| *A61B 5/026* | (2006.01) |

(52) U.S. Cl.
CPC ........... *G02B 13/24* (2013.01); *G02B 27/286* (2013.01); *G02B 27/30* (2013.01); *G06F 3/0412* (2013.01); *G06F 3/0421* (2013.01); *G06K 9/0004* (2013.01); *G06K 9/00013* (2013.01); *G06K 9/00026* (2013.01); *H01L 27/3234* (2013.01); *H04N 5/2253* (2013.01); *H04N 5/2254* (2013.01); *A61B 5/0261* (2013.01); *A61B 5/14552* (2013.01); *G02B 2207/123* (2013.01); *G06F 2203/0338* (2013.01); *G06F 2203/04103* (2013.01); *G06K 9/0008* (2013.01); *G06K 2009/0006* (2013.01); *G06K 2009/00939* (2013.01)

(58) Field of Classification Search
CPC .... H04N 5/2254; H04N 5/2253; G02B 27/30; G02B 27/286; H01L 27/3234; G06F 2203/041; G06F 3/0412; A61B 5/14552; A61B 5/1172
See application file for complete search history.

(56) References Cited

U.S. PATENT DOCUMENTS

| | | | |
|---|---|---|---|
| 7,697,053 B2 | 4/2010 | Kurtz et al. | |
| 7,808,540 B2 | 10/2010 | Cok | |
| 8,593,503 B2 | 11/2013 | Bolle | |
| 8,994,690 B2 | 3/2015 | Shi et al. | |
| 9,829,614 B2 | 11/2017 | Smith et al. | |
| 2004/0164953 A1 | 8/2004 | Keranen et al. | |
| 2004/0252867 A1* | 12/2004 | Lan | G06K 9/0004 382/124 |
| 2004/0263670 A1 | 12/2004 | Yamasaki | |
| 2006/0007222 A1 | 1/2006 | Uy | |
| 2009/0141116 A1 | 6/2009 | Kanade et al. | |
| 2010/0034433 A1 | 2/2010 | Thiebot et al. | |
| 2010/0066800 A1 | 3/2010 | Ryf et al. | |
| 2011/0102308 A1 | 5/2011 | Nakamura et al. | |
| 2011/0102569 A1 | 5/2011 | Erhart | |
| 2011/0285680 A1 | 11/2011 | Nakamura | |
| 2012/0113160 A1 | 5/2012 | Kurokawa | |
| 2012/0162490 A1 | 6/2012 | Chung | |
| 2012/0167170 A1 | 6/2012 | Shi et al. | |
| 2013/0135268 A1 | 5/2013 | Kanade et al. | |
| 2013/0135328 A1 | 5/2013 | Rappoport et al. | |
| 2013/0287272 A1 | 10/2013 | Lu et al. | |
| 2013/0287274 A1 | 10/2013 | Shi et al. | |
| 2013/0293459 A1 | 11/2013 | Nakamura et al. | |
| 2014/0016071 A1 | 1/2014 | Yang et al. | |
| 2014/0037257 A1 | 2/2014 | Yang et al. | |
| 2014/0092028 A1 | 4/2014 | Prest et al. | |
| 2014/0092346 A1 | 4/2014 | Yang et al. | |
| 2014/0129843 A1 | 5/2014 | Shi et al. | |
| 2014/0218327 A1 | 8/2014 | Shi et al. | |
| 2014/0292666 A1 | 10/2014 | Shi et al. | |
| 2015/0036065 A1 | 2/2015 | Yousefpor et al. | |
| 2015/0109214 A1 | 4/2015 | Shi et al. | |
| 2015/0154436 A1 | 6/2015 | Shi et al. | |
| 2015/0331508 A1 | 11/2015 | Nho et al. | |
| 2015/0347813 A1 | 12/2015 | Tsen | |
| 2015/0379323 A1 | 12/2015 | Erhart et al. | |
| 2016/0132712 A1* | 5/2016 | Yang | G06K 9/0002 348/77 |
| 2016/0224816 A1 | 8/2016 | Smith et al. | |
| 2016/0247010 A1 | 8/2016 | Huang et al. | |
| 2017/0156651 A1 | 6/2017 | Arias | |

FOREIGN PATENT DOCUMENTS

| | | |
|---|---|---|
| WO | WO 2015041459 A1 | 3/2016 |
| WO | WO 2016015009 A1 | 3/2016 |

OTHER PUBLICATIONS

Lochner, Claire M., et al. "All-organic optoelectronic sensor for pulse oximetry." *Nature communications* 5 Article No. 5745, DOI: 10.1038/ncomms6745, Dec. 10, 2014.

English translation of CN102073860 submitted with Third Party Submission under 37 CFR 1.290 in U.S. Appl. No. 15/199,774, on Oct. 26, 2017.

Claire M. Lochner et al., All-organic optoelectronic sensor for pulse oximetry, Nature Communications, Dec. 10, 2014, Macmillan Publishers Limited.

* cited by examiner

COMPOUND COLLIMATING SYSTEM USING APERTURES AND COLLIMATORS

CROSS-REFERENCE TO RELATED APPLICATIONS

This patent application claims the benefit of U.S. Provisional Patent Application No. 62/289,172, filed Jan. 29, 2016, which is incorporated by reference. This patent application is also related to U.S. patent application Ser. No. 15/199,774, filed Jun. 30, 2016, which is incorporated by reference.

BACKGROUND

Input devices, including touch sensor devices (also commonly called touchpads or proximity sensor devices), as well as fingerprint sensor devices, are widely used in a variety of electronic systems.

Touch sensor devices typically include a sensing region, often demarked by a surface, in which the touch sensor device determines the presence, location and/or motion of one or more input objects, typically for purposes allowing a user to provide user input to interact with the electronic system.

Fingerprint sensor devices also typically include a sensing region in which the fingerprint sensor device determines presence, location, motion, and/or features of a fingerprint or partial fingerprint, typically for purposes relating to user authentication or identification of a user.

Touch sensor devices and fingerprint sensor devices may thus be used to provide interfaces for the electronic system. For example, touch sensor devices and fingerprint sensor devices are often used as input devices for larger computing systems (such as opaque touchpads and fingerprint readers integrated in or peripheral to notebook or desktop computers). Touch sensor devices and fingerprint sensors are also often used in smaller computing systems (such as touch screens integrated in mobile devices such as smartphones and tablets).

SUMMARY

In an exemplary embodiment, an optical sensor system having a compound aperture and collimator structure for collimating light includes: an input surface providing a sensing region for a biometric object; an aperture layer, disposed beneath the input surface; a plurality of light-blocking structures, disposed beneath the aperture layer, forming a plurality of collimators; and an image sensor, disposed beneath the plurality of light-blocking structures, wherein the image sensor is configured to detect light from the sensing region that has passed through the aperture layer and the plurality of collimators.

In another exemplary embodiment, an optical sensor system having a compound aperture and collimator structure for collimating light includes: an input surface providing a sensing region for a biometric object; a color layer, comprising a plurality of apertures, disposed beneath the input surface; a plurality of light-blocking structures, disposed beneath the color layer; and an image sensor, disposed beneath the plurality of light-blocking structures, wherein the image sensor is configured to detect light from the sensing region that has passed through the aperture layer.

In yet another exemplary embodiment, a method for producing an optical biometric sensor having a compound aperture and collimator structure for collimating light includes: forming a plurality of collimators over an image sensor, wherein the plurality of collimators are formed by a plurality of light blocking structures; forming a transparent layer over the plurality of collimators; and forming an aperture layer over the transparent layer, wherein the aperture layer comprises a plurality of apertures aligned to the plurality of collimators.

In yet another exemplary embodiment, an optical sensor system having a compound aperture and collimator structure for collimating light includes: an aperture layer; a transparent layer, disposed beneath the aperture layer; a plurality of light-blocking structures, disposed beneath the transparent layer, forming a plurality of collimators; and an image sensor, disposed beneath the plurality of light-blocking structures, wherein the image sensor is configured to detect light from a sensing region for a biometric object above the aperture layer, wherein the detected light has passed from the sensing region through the aperture layer and the plurality of collimators.

DETAILED DESCRIPTION

The following detailed description is exemplary in nature and is not intended to limit the disclosure or the application and uses of the disclosure. Furthermore, there is no intention to be bound by any expressed or implied theory presented in the preceding background and brief description of the drawings, or the following detailed description.

Exemplary embodiments of this disclosure provide for light collimation using a compound collimating system having an aperture layer and a collimator filter layer. By using an aperture layer together with a collimator filter layer, various advantages are achieved with respect to achieving a relatively high aspect ratio for an optical sensing system using a cost-effective structure that is relatively easy to manufacture.

Figure 1:
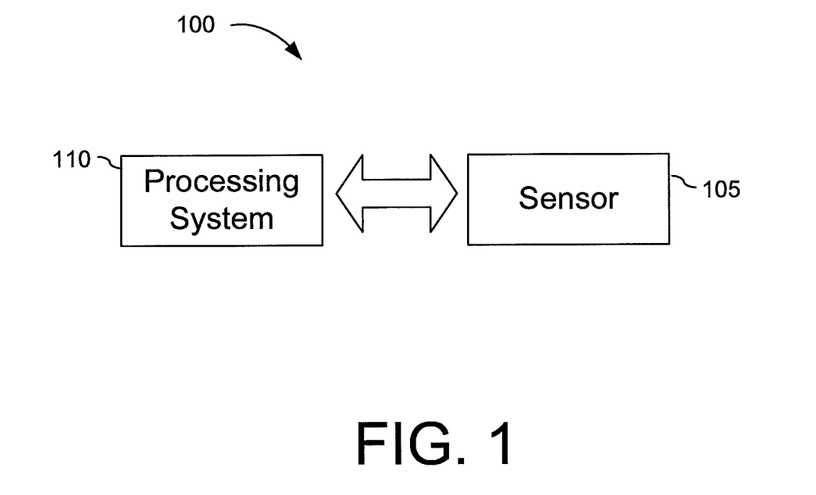
FIG. 1 is a block diagram of an example input device.

FIG. 1 is a block diagram of an example input device 100. The input device 100 may be configured to provide input to an electronic system (not shown). As used in this document, the term "electronic system" (or "electronic device") broadly refers to any system capable of electronically processing information. Some non-limiting examples of electronic systems include personal computers of all sizes and shapes, such as desktop computers, laptop computers, netbook computers, tablets, web browsers, e-book readers, personal digital assistants (PDAs), and wearable computers (such as smart watches and activity tracker devices). Additional examples of electronic systems include composite input devices, such as physical keyboards that include input device 100 and separate joysticks or key switches. Further examples of electronic systems include peripherals such as data input devices (including remote controls and mice), and data output devices (including display screens and printers). Other examples include remote terminals, kiosks, and video game machines (e.g., video game consoles, portable gaming devices, and the like). Other examples include communication devices (including cellular phones, such as smart phones), and media devices (including recorders, editors, and players such as televisions, set-top boxes, music players, digital photo frames, and digital cameras). Additionally, the electronic system could be a host or a slave to the input device.

The input device 100 can be implemented as a physical part of the electronic system, or can be physically separate from the electronic system. As appropriate, the input device 100 may communicate with parts of the electronic system using any one or more of the following: buses, networks, and other wired or wireless interconnections. Examples include I2C, SPI, PS/2, Universal Serial Bus (USB), Bluetooth, RF, and IRDA.

In FIG. 1, a sensor 105 is included with the input device 100. The sensor 105 comprises one or more sensing elements configured to sense input provided by one or more input objects in a sensing region. Examples of input objects include fingers, styli, and hands. Sensing region encompasses any space above, around, in and/or near the sensor 105 in which the input device 100 is able to detect user input (e.g., user input provided by one or more input objects). The sizes, shapes, and locations of particular sensing regions may vary from embodiment to embodiment. In some embodiments, the sensing region extends from a surface of the input device 100 in one or more directions into space until signal-to-noise ratios prevent sufficiently accurate object detection. The distance to which this sensing region extends in a particular direction, in various embodiments, may be on the order of less than a millimeter, millimeters, centimeters, or more, and may vary significantly with the type of sensing technology used and the accuracy desired. Thus, some embodiments sense input that comprises no contact with any surfaces of the input device 100, contact with an input surface (e.g., a touch surface) of the input device 100, contact with an input surface of the input device 100 coupled with some amount of applied force or pressure, and/or a combination thereof. In various embodiments, input surfaces may be provided by surfaces of sensor substrates within which or on which sensor elements are positioned, or by face sheets or other cover layers positioned over sensor elements.

The input device 100 may utilize optical sensing techniques where one or more sensing elements detect light from the sensing region. The detected light may be reflected from the input object, transmitted through the input object, emitted by input object, or some combination thereof. The detected light may be in the visible or invisible spectrum (such as infrared or ultraviolet light). Example optical sensing elements include photodiodes, CMOS image sensor arrays, CCD arrays, photodiodes, and other suitable photosensors sensitive to light in wavelength(s) of interest. Active illumination may be used to provide light to the sensing region, and reflections from the sensing region in the illumination wavelength(s) may be detected to determine input information corresponding to the input object.

One example optical technique utilizes direct illumination of the input object, which may or may not be in contact with an input surface of the sensing region depending on the configuration. One or more light sources and/or light guiding structures are used to direct light to the sensing region. When an input object is present, this light is reflected directly from surfaces of the input object, which reflections can be detected by the optical sensing elements and used to determine input information about the input object.

Another example optical technique utilizes indirect illumination based on internal reflection to detect input objects in contact with an input surface of the sensing region. One or more light sources are used to direct light in a transmitting medium at an angle at which it is internally reflected at the input surface of the sensing region, due to different refractive indices at opposing sides of the interface defined by the input surface. Contact of the input surface by the input object causes the refractive index to change across this boundary, which alters the internal reflection characteristics at the input surface. Higher contrast signals can often be achieved if principles of frustrated total internal reflection (FTIR) are used to detect the input object, where the light is directed to the input surface at an angle of incidence at which it is totally internally reflected, except at locations where the input object is in contact and causes the light to partially transmit across this interface. An example of this is presence of a finger introduced to an input surface defined by a glass to air interface. The higher refractive index of human skin compared to air causes light incident at the input surface at the critical angle of the interface to air to be partially transmitted through the finger, where it would otherwise be totally internally reflected at the glass to air interface. This optical response can be detected by the system and used to determine spatial information. In some embodiments, this can be used to image small scale surface variations of the input object, such as fingerprint patterns, where the internal reflectivity of the incident light differs depending on whether a ridge or valley of the finger is in contact with that portion of the input surface.

In FIG. 1, a processing system 110 is included with the input device 100. The processing system 110 comprises parts of or all of one or more integrated circuits (ICs) and/or other circuitry components. The processing system 110 is coupled to the sensor 105, and is configured to detect input in the sensing region using sensing hardware of the sensor 105.

The processing system 110 may include driver circuitry configured to drive sensing signals with sensing hardware of the input device 100 and/or receiver circuitry configured to receive resulting signals with the sensing hardware. For example, a processing system for an optical sensor device may comprise driver circuitry configured to drive illumination signals to one or more LEDs or other light sources, and/or receiver circuitry configured to receive signals with optical receiving elements.

The processing system 110 may include electronically-readable instructions, such as firmware code, software code, and/or the like. The processing system 110 can be implemented as a physical part of the sensor 105, or can be physically separate from the sensor 105. Also, constituent components of the processing system 110 may be located together, or may be located physically separate from each other. For example, the input device 100 may be a peripheral coupled to a computing device, and the processing system 110 may comprise software configured to run on a central processing unit of the computing device and one or more ICs (e.g., with associated firmware) separate from the central processing unit. As another example, the input device 100 may be physically integrated in a mobile device, and the processing system 110 may comprise circuits and firmware that are part of a main processor of the mobile device. The processing system 110 may be dedicated to implementing the input device 100, or may perform other functions, such as operating display screens, driving haptic actuators, etc.

The processing system 110 may operate the sensing element(s) of the input device 100 to produce electrical signals indicative of input (or lack of input) in a sensing region. The processing system 110 may perform any appropriate amount of processing on the electrical signals in producing the information provided to the electronic system. For example, the processing system 110 may digitize analog electrical signals obtained from the sensor electrodes. As another example, the processing system 110 may perform filtering or other signal conditioning. As yet another example, the processing system 110 may subtract or otherwise account for a baseline, such that the information reflects a difference between the electrical signals and the baseline. As yet further examples, the processing system 110 may determine positional information, recognize inputs as commands, recognize handwriting, match biometric samples, and the like.

The sensing region of the input device 100 may overlap part or all of an active area of a display device, for example, if the sensor 105 provides a touch screen interface. The display device may be any suitable type of dynamic display capable of displaying a visual interface to a user, including an inorganic light emitting diode (LED) display, organic LED (OLED) display, cathode ray tube (CRT), liquid crystal display (LCD), plasma display, electroluminescence (EL) display, or other display technology. The display may be flexible or rigid, and may be flat, curved, or have other geometries. The display may include a glass or plastic substrate for TFT circuitry, which may be used to address display pixels for providing visual information and/or providing other functionality. The display device may include a cover lens (sometimes referred to as a "cover glass") disposed above display circuitry and above inner layers of the display module, and the cover lens may also provide an input surface for the input device 100. Examples of cover lens materials include optically clear amorphous solids, such as chemically hardened glass, and optically clear crystalline structures, such as sapphire. The input device 100 and the display device may share physical elements. For example, some of the same electrical components may be utilized for both displaying visual information and for input sensing with the input device 100, such as using one or more display electrodes for both display updating and input sensing. As another example, the display screen may be operated in part or in total by the processing system 110 in communication with the input device.

Figure 2A:
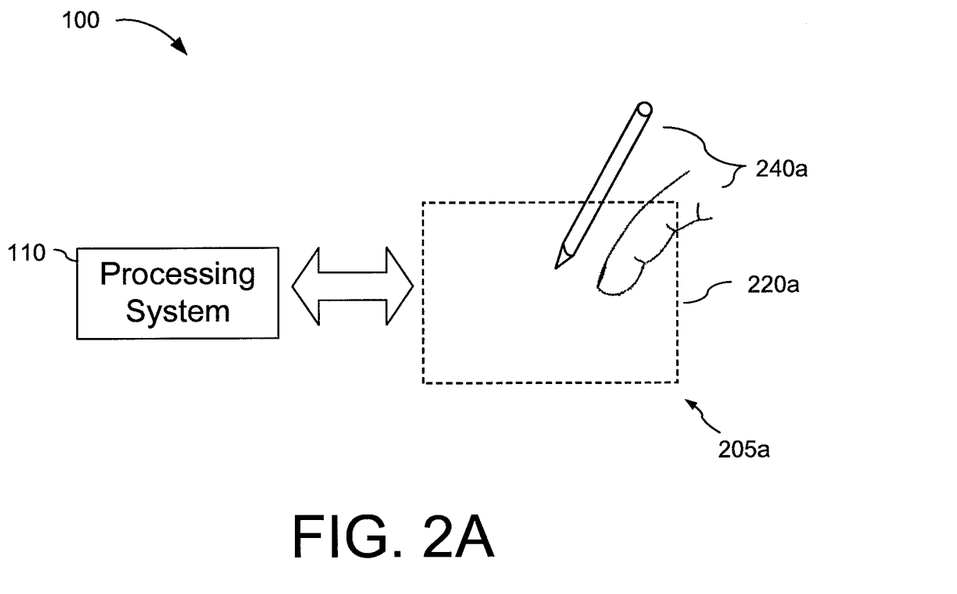
FIG. 2A is a block diagram of another example input device.
Figure 2B:
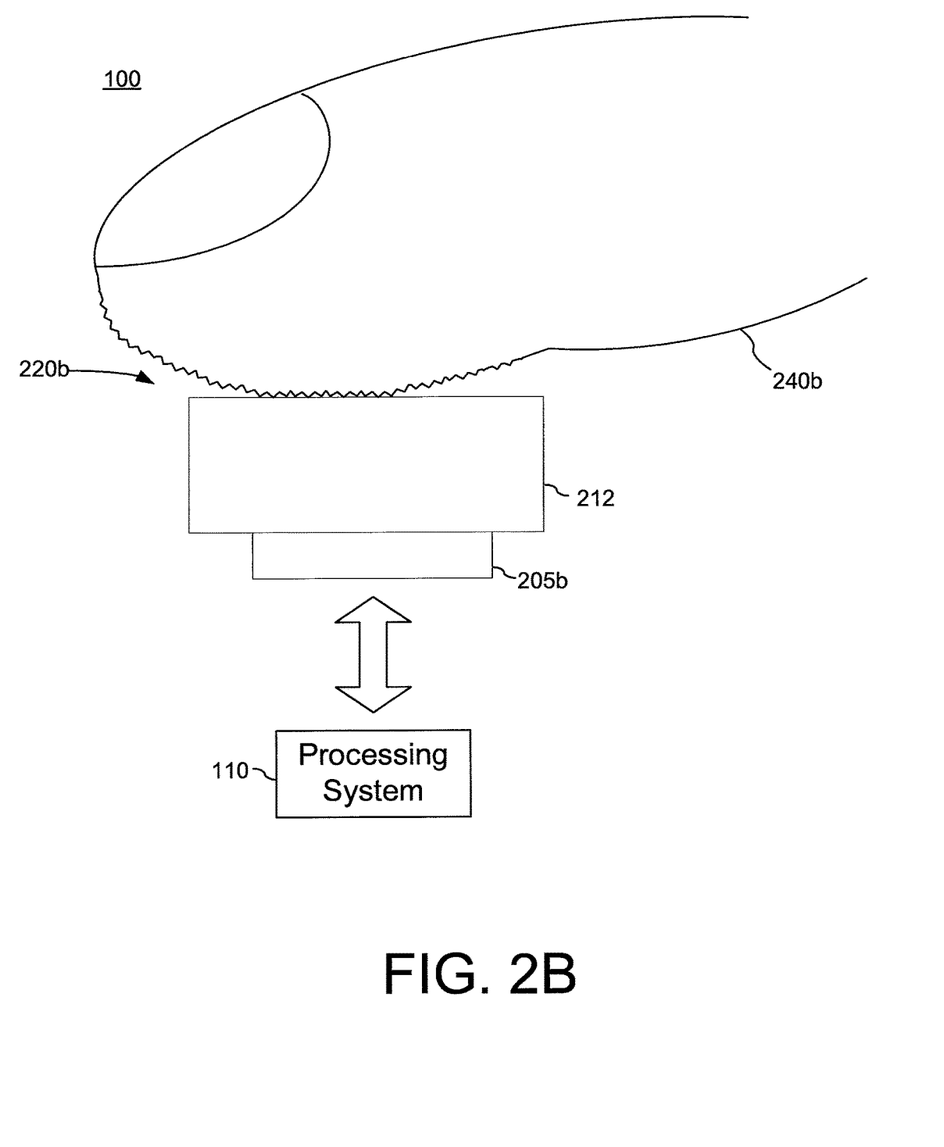
FIG. 2B is a block diagram of another example input device.

FIGS. 2A-2B depict further example input devices 100. In FIG. 2A, the input device 100 is shown as including a touch sensor 205a. The touch sensor 205a is configured to detect position information of an input object 240a within the sensing region 220a. The input object 240a may include a finger or a stylus, as shown in FIG. 2A. The sensing region 220a may include an input surface having a larger area than the input object. The touch sensor 205a may include an array of sensing elements with a resolution configured to detect a location of a touch to the input surface.

In FIG. 2B, the input device 100 is shown as including a fingerprint sensor 205b. The fingerprint sensor 205b is configured to capture a fingerprint from a finger 240b. The sensor 205b is disposed underneath a cover layer 212 that provides an input surface for the fingerprint to be placed on or swiped over the sensor 205b. The sensing region 220b may include an input surface with an area larger than, smaller than, or similar in size to a full fingerprint. The fingerprint sensor 205b has an array of sensing elements with a resolution configured to detect surface variations of the finger 240b, and the fingerprint sensor 205b has a higher resolution than the touch sensor 205a of FIG. 2A.

Figure 3A:
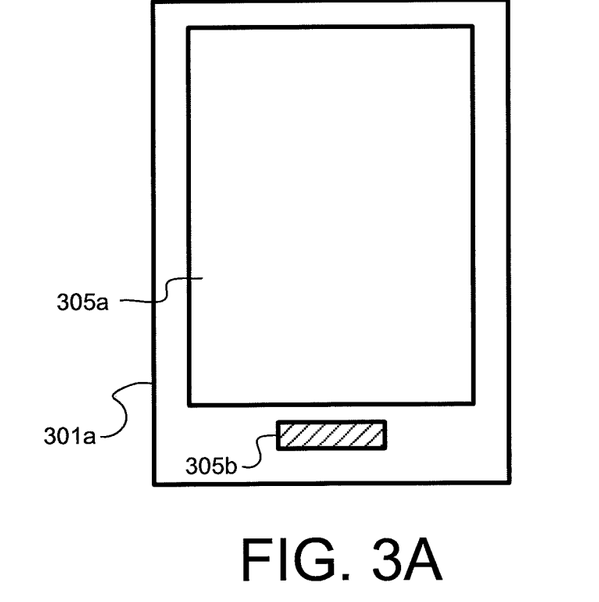
FIGS. 3A-3B are block diagrams illustrating example electronic devices having both a touch screen interface and a fingerprint sensing interface.
Figure 3B:
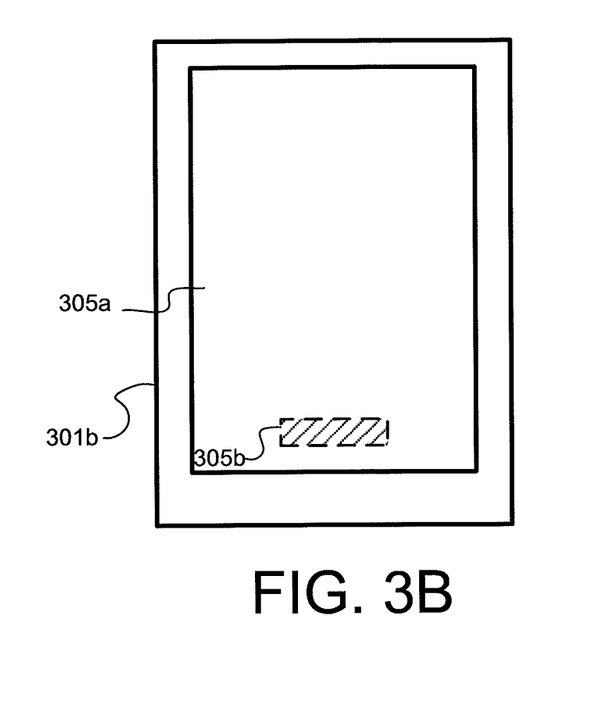

FIGS. 3A-3B are block diagrams illustrating example electronic devices 301a and 301b having both a display and a fingerprint sensing interface. In FIG. 3A, the electronic device (e.g., a mobile device, such as a smartphone or tablet) 301a has a fingerprint sensor 305b that is separate from the active display area 305a. In FIG. 3B, the electronic device 301b has a fingerprint sensor 305b that is integrated within the active display area 305a, such that the interface for the fingerprint sensor overlaps with the interface for the touch sensor. In FIGS. 3A-3B, a touch sensor interface may also overlap with the active area of the display, such that in FIG. 3B the active display area includes both a fingerprint sensing and touch sensing interface.

The configuration in FIG. 3B is desirable as it allows removal of a home button located on the front cover glass, providing opportunities for both improved cosmetic design and increasing display area. To achieve the configuration in FIG. 3B, in some embodiments, an optical fingerprint sensor (OFPS) may be placed under a semi-transparent display, with an aperture layer in and/or below the semi-transparent display and a collimator for providing relatively improved optical resolution.

As depicted in FIGS. 3A-3B, an exemplary application for embodiments of the disclosure is a fingerprint sensor for a mobile device. While enhanced fingerprint imaging through thicker material stacks (e.g., cover glass, touch sensor, adhesives and display) may be made possible by collimating light directly above an optical fingerprint sensor (OFPS) to provide a given aspect ratio defined by the dimensions of a collimator (i.e., column height:column opening), manufacturing collimators with high aspect ratios (such as 15:1 or greater) can be costly or impracticable, as collimator costs become increasingly higher and manufacturing becomes increasingly difficult and/or impossible as the aspect ratio increases.

Exemplary embodiments of the disclosure, however, allow for an optical fingerprint sensor to be provided for various applications (including under the display of a mobile device or on a non-display part of a mobile device) by utilizing a compound collimating system having an aperture layer to be used in combination with a collimator filter layer. This reduces the collimator cost for a given optical resolution and helps to mitigate or eliminate cross-talk between pixels of the optical sensor. Further, in addition to reduced cost, reduced thickness may also be achieved, as well as providing an improved effective aspect ratio.

Figure 4:
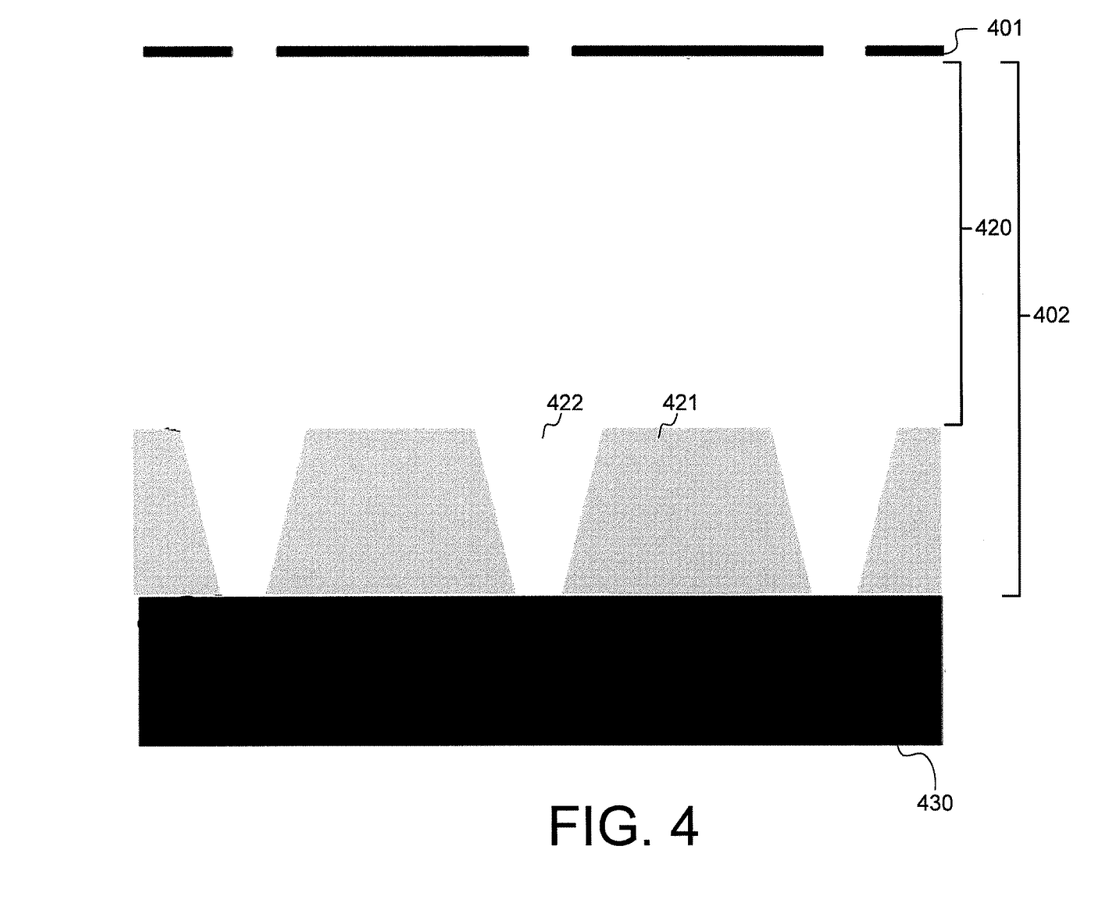
FIG. 4 is a block diagram of an example optical fingerprint sensor with a compound collimating system having an aperture layer and a collimating filter layer.

FIG. 4 is a block diagram of an example optical fingerprint sensor with an aperture layer 401 and a collimating filter layer 402. An input surface for a biometric object (e.g., a fingerprint), which is not depicted in FIG. 4, is provided above the aperture layer 401 (e.g., above a cover glass or cover lens or other protective layer, which is also not depicted in FIG. 4). The collimating filter layer 402 is disposed beneath the aperture layer 401, and the collimating filter layer 402 may include a gap or a transparent layer (e.g., glass) 420 and a plurality of light-blocking structures 421 forming a plurality of collimators having collimating areas 422. The collimating areas 422 formed between the light-blocking structures 421 may be similar to the array of light collimating apertures or holes as described in U.S. patent application Ser. No. 14/871,810, filed Sep. 30, 2015, to SMITH et al., entitled "OPTICAL SENSOR USING COLLIMATOR," the entire contents of which are hereby incorporated by reference herein.

An image sensor 430 is further provided below the plurality of light-blocking structures 421. The image sensor 430 may be, for example, a CMOS image sensor (CIS) comprising a plurality of light-sensing elements corresponding to pixels of the image sensor 430, with respective light-sensing elements or pixels being aligned to collimating areas 422. In other exemplary implementations, the apertures and corresponding collimators aligned to the apertures may not be aligned to a bottom optical CMOS sensor. For example, the density of pixels in the image sensor 430 may be greater than the density of collimating areas 422. In this case, precise alignment between collimating areas 422 and pixels in the image sensor 430 may not be needed, as multiple pixels may capture the light from a single collimating area 422.

In an exemplary embodiment, the aperture layer 401 may be a film, such as an Aluminum film or a film of some other metal or light-blocking materials, formed on top of a glass layer 420. Further, the aperture layer 401 may be formed of a reflective material to help with delivering and reflecting light more efficiently with respect to an input object being sensed by the optical sensor.

The light blocking structures 421 may be formed of etched silicon or a variety of other suitable materials, including plastics such as polycarbonate, PET, polyimide, carbon black, inorganic insulating or metallic materials, or SU-8. The collimating areas 422 may be filled with air or a transparent material. Also, the light blocking structures 421 may be made of one layer, such as silicon with high aspect ratio holes drilled through, or several stacked layers with openings aligned with each other to collectively form a higher aspect ratio light collimating area.

In one exemplary implementation where an optical sensor having the features shown in FIG. 4 is provided in a display device, the aperture layer 401 may be provided as part of or under a display stack of the device. In another exemplary implementation where an optical sensor having the features shown in FIG. 4 is provided in a display device, the aperture layer 401 may be part of an optical sensor package that is under a display stack of the device. In another exemplary implementation where an optical sensor having the features shown in FIG. 4 is provided in a display device, the aperture layer 401 and the other features illustrates in FIG. 4 may be located apart from a display of the display device (i.e., not under a display stack). In other exemplary implementations, an optical sensor having the features shown in FIG. 4 may be provided in a non-display device.

For a given optical resolution, using a combined aperture layer and collimator structure (i.e., the combination of aperture layer 401 and collimating filter layer 402) reduces the thickness needed for light-blocking structures 421 relative to an optical sensor having a collimating filter layer without an aperture layer (in which case the thickness of the light-blocking structures would need to cover the full distance between the aperture layer 401 and the light sensing elements 430 depicted in FIG. 4). The reduction in collimator thickness can also reduce collimator cost. Due to cost and constraints in manufacturing, an optical sensor structure having an aperture layer in combination with a collimator filter layer enables higher effective aspect ratios relative to an optical sensor structure relying only on collimators.

The aperture layer 401 includes an array of openings or apertures. The openings (or "apertures") of the aperture layer 401 may be aligned to the openings in the collimator filter layer 402 corresponding to the collimating areas 422. These apertures may be referred to as "primary" and/or "entrance" apertures for the compound collimating system formed by the combination of the aperture layer 401 and the collimating filter layer 402.

In an exemplary embodiment, the plurality of light-blocking structures 421 with collimating areas 422 are formed using etched silicon having a thickness of up to 100 µm or up to 105 µm (which provides for relative ease of manufacture), and the combination of the aperture layer 401 with the collimating filter layer 402 provides an aspect ratio of 15:1 or greater (e.g., including 20:1 or 30:1). Further, as can be seen based on the shape of light-blocking structures 421, cross-talk between pixels of the optical sensor (i.e., corresponding to light sensing elements 430) is prevented. The size D of primary apertures in the aperture layer 401 (whether in a TFT layer of a display or a standalone aperture layer) may be chosen to be sufficiently large that the Fraunhofer Distance R ($R \sim 2*D^2/\lambda$) is close to the distance from the aperture layer 401 to the top of the light-blocking structures 421. This allows the primary apertures to be made as small as possible, increasing the optical resolution by increasing the aspect ratio, without incurring the loss of resolution associated with diffraction at the primary apertures.

In one example having the structure shown in FIG. 4, the size of the primary entrance apertures of the aperture layer 401 may be approximately 10 µm holes, with the top diameters for the collimating areas being approximately 40 µm (or less) and the bottom diameters for the collimating areas being approximately 10 µm (e.g., 10 µm±1 µm). Further, in this example, the aperture layer 401 may, for example, be a 100 nm thick Aluminum light-blocking layer; the gap or transparent layer 420 may be 145 µm thick, and the light-blocking structures 421 may be etched silicon structures having a height of 105 µm. The alignment tolerance between collimating layer and image sensor may be ±7 µm, and the alignment tolerance between aperture layer and collimating layer may be ±15 µm, but this may vary depending on the particular materials and manufacturing processes used, as well as the optical design.

In an exemplary implementation, the spaces between the light-blocking structures 421 (i.e., collimating regions 422) may be filled with the same material that is used for the gap or transparent layer 420 to provide for relatively simple manufacturing and improved stray light rejection properties for the compound collimating system. For example, if the gap or transparent layer 420 is an air gap, the collimating areas 422 may also be empty spaces occupied by air. In another example, if the gap or transparent layer 420 is glass, such as a glass with a low index of refraction, the collimating areas 422 may be filled with the same type of glass.

In an exemplary embodiment, the collimating areas 422 are aligned to light-sensing elements of the image sensor 430, and are also aligned to the primary entrance apertures of the aperture layer 401.

In an exemplary embodiment, the light-blocking structures 421 may be formed such that the walls defining the respective collimating areas are slanted (or "tapered"), as depicted, for example, in FIG. 4. In other exemplary embodiments, the light-blocking structures 421 may be formed with vertical walls. In practice, it may be advantageous to utilize light-blocking structures having slanted or tapered sidewalls for ease of manufacture and to allow for more tolerance with respect to alignment. Further, it will be appreciated that for an optical sensor system that relies only on etched silicon collimators (i.e., which does not have the compound aperture layer plus collimator filter layer structure depicted in FIG. 4), the option to use slanted or tapered sidewalls is not possible or severely limited (since aspect ratio is defined solely by shape of the collimating areas between the light blocking structures). In contrast, for an optical sensor system utilizing the compound collimating system structure depicted in FIG. 4, the aspect ratio is defined by the size of the apertures in the aperture layer 401 in combination with the shape of the collimating areas 422 (since the apertures in the aperture layer 401 restricts certain angles of light from entering the collimating areas 422, the size of the tops of collimating areas 422 can be significantly larger than the size of the bottoms of the collimating areas 422). The size of the tops of the collimating areas 422 can also be larger than the size of the entrance apertures in the aperture layer 401, allowing greater tolerance for alignment between aperture layer and the plurality of collimators.

In certain exemplary embodiments, the openings at tops of collimators may have a larger diameter than apertures in the aperture layer, and openings at bottoms of collators may have a diameter smaller than apertures in the aperture layer, as well as smaller than openings at the tops of collimators. This provides, for example, certain advantages with respect to ease of manufacture and alignment tolerance.

It will be appreciated that different embodiments may utilize different apertures shapes for the apertures of the aperture layer. For example, in one exemplary embodiment, the primary entrance apertures may be circular. In another exemplary embodiment, the primary entrance apertures may be non-circular, such as rectangular or square-shaped apertures.

Although not depicted in FIG. 4, the optical sensor system further includes a light source for illuminating a sensing region on or above the input surface. In exemplary embodiments where the optical sensor is part of a display device, display elements of a display (e.g., light-emitting diodes (LEDs) or organic light-emitting diodes (OLEDs) that are also used to provide the display) may, for example, serve as the light source. In other exemplary embodiments, an auxiliary light source (e.g., one or more discrete LEDs or OLEDs) may be used instead of or in addition to the display as a light source for illuminating the finger. The auxiliary light source may, for example, directly illuminate the fingerprint or may provide light that is directed into the cover glass to utilize the cover glass as a light guide for total internal reflection (TIR) mode illumination. In further exemplary embodiments, environmental or ambient light may be used to illuminate the finger (e.g., sunlight may pass through the finger and be refracted by the fingerprint features), in which case no active illumination of the fingerprint or sensing region is needed. In various implementations, light from the sensing region that is detected by the sensor may be reflected, refracted, or scattered by the biometric object to affect the resulting image captured by the sensor. The light source may also be provided as part of an illumination layer, and, in a display application, the illumination layer may be part of or separate from a display stack.

Figure 5:
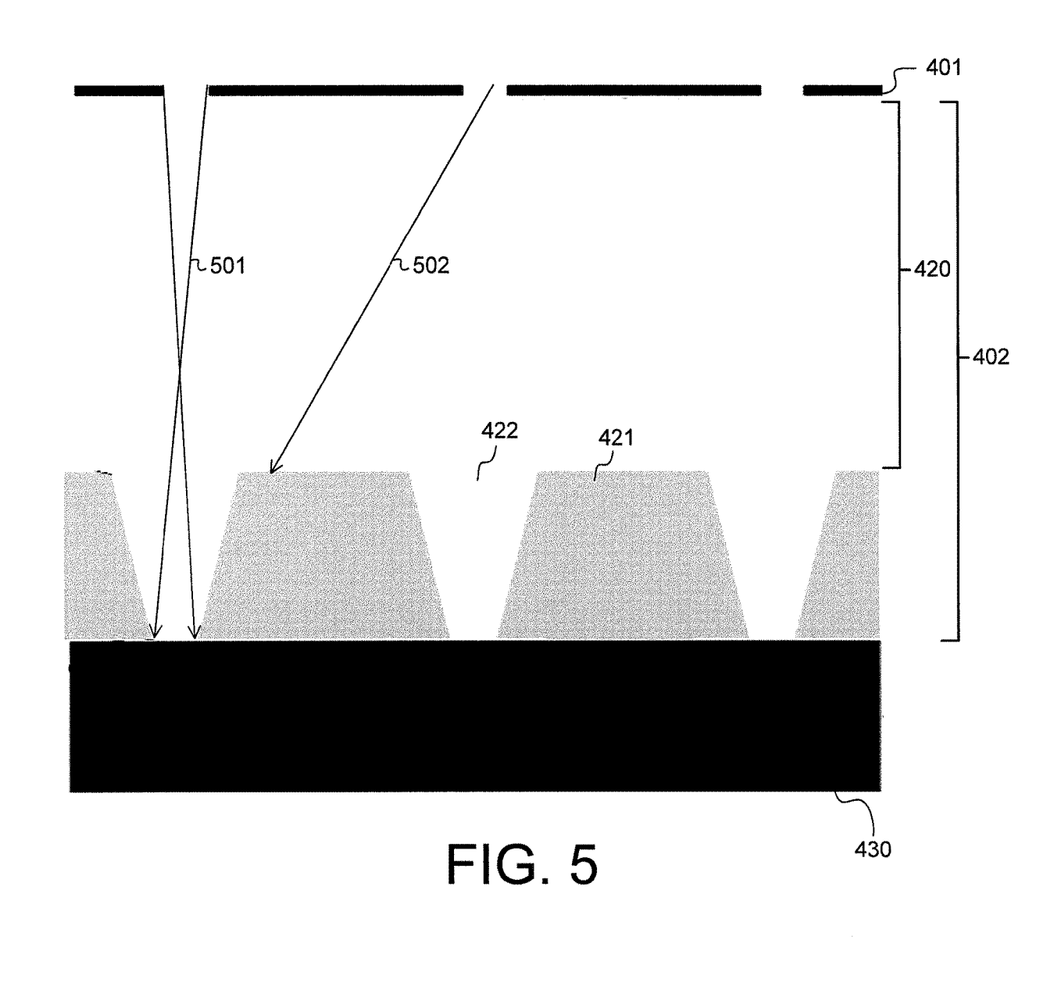
FIG. 5 is a block diagram of the example optical fingerprint sensor from FIG. 4 with exemplary light rays illustrating the function of the aperture layer 401 and the collimating filter layer 402.

FIG. 5 is a block diagram of the example optical fingerprint sensor from FIG. 4 with exemplary light rays illustrating the function of the aperture layer 401 and the collimating filter layer 402. As can be seen from desired light rays 501, the aperture layer 401 in combination with the collimating filter layer 402, form an effective compound collimating structure having an aspect ratio defined by the dimensions of the apertures and the shape of the collimating areas 422. Further, the light-blocking structures 421 restrict cross-talk by blocking stray light, which, for example, may be light that is not transmitted through a respective aperture and collimator aligned with a light sensing element of the image sensor 430 (e.g., stray light ray 502 transmitted through the middle aperture in FIG. 5 is directed at a light sensing element aligned with the aperture and collimator at the left side of FIG. 5, and is blocked by a light-blocking structure 421, preventing cross-talk due to stray light ray 502).

In certain exemplary embodiments, the light-blocking structures 421 forming the collimators are bonded to an image sensor chip 430. It may thus be desirable to use a materials for the light-blocking structures 421 and the collimating areas 422 that has a similar thermal expansion coefficient (CTE) as the image sensor chip, such as silicon or glass.

In certain exemplary embodiment, wafer-level processing is desirable for high yield and reproducible precision alignment in manufacture.

In an exemplary embodiment, the manufacturing process for an optical sensor having a compound collimating system using apertures and collimators as depicted in FIG. 4 includes forming the apertures of the aperture layer 401 on a glass layer 420 after the glass layer 420 is bonded to the etched silicon layer of the plurality of light-blocking structures 421. By forming the apertures on the glass after the glass is bonded to the silicon, the alignment tolerance during the glass bonding is very large and easy to achieve, simplifying the manufacturing process. Further, alignment of the top aperture patterns (i.e., the apertures of the aperture layer 401) can be registered to fiducials on either the silicon layer (in which the light-blocking structures 421 are disposed) or on the bottom of a CMOS wafer.

In various different embodiments, different material sets and process flows may be used to fabricate a device having an optical sensor with a compound collimating system having apertures and collimators. In an example, the top aperture layer may be formed with a metal, with the metal also being used as a capacitive touch sensor, for example, to either detect the presence of a finger or the motion of the finger, or to perform other functions. The material for the top layer may be selected to block any desired wavelength(s) of interest (i.e., the wavelength(s) used for imaging the input object), including, for example, polymers and metals. The transparent layer may be glass or any plastic that is transparent to the wavelength(s) of interest. The light-blocking structures forming the collimators may be, for example, silicon, and the collimating areas between the light-blocking structure may be holes in the silicon formed by wet or dry etches, or by laser. Alternatively, the light-blocking structures in the forming the collimators may be, for example, an absorbing polymer with the collimating areas being holes in the absorbing polymer formed by laser drilling.

As discussed above, embodiments of the disclosure may be used with respect to display applications as well as non-display applications, and with respect to display applications, the compound collimating system (and the optical sensor corresponding thereto) may be located in a portion of a display device under a display or in a portion of the display device not under the display. In situations where optical sensor is not located under a display (whether in a display device or non-display device), challenges may arise from attempting to locate the optical sensor under a colored layer (such as a colored ink layer or a colored metal layer). For example, it may be difficult to place an optical sensor under a white color layer (such as a white ink layer) or bright color layer having white color mixed in due to scattering caused by the white color, or under a non-white color layer (such as a black ink layer) due to absorption caused by the non-white color. Further, for aesthetic purposes, a consistent look and feel may be desired such that the appearance of the color layer above the optical sensor should be the same as the appearance of color layer in other portions of the device (e.g., for a mobile device, a consistent color such as white or black may be desired all around the display portion of the device even when there is an optical sensor located within the device outside the display portion of the device).

Further exemplary embodiments of the disclosure provide an aperture layer in or proximate to a color layer of the device to be used with the compound collimating system discussed above. In one exemplary configuration, by providing a semi-transparent color layer, and by providing the aperture layer as a reflective layer or a dark (or substantially opaque) layer beneath the semi-transparent color layer, a consistent look and feel for the appearance of the color layer above an optical sensor having the compound collimating system may be achieved (a reflective layer provides for a white or bright appearance consistent with other white or bright portions of a white or bright color layer due to its reflective properties, and a dark layer provides for a richer or darker appearance consistent with other non-white or dark portions of a non-white or dark color layer due to its absorptive properties). In another exemplary configuration, the apertures of the aperture layer may be formed in the color layer itself, for example, by patterning of a color ink layer. It will be appreciated that the apertures, which may be for example 10 μm holes, can be substantially unnoticeable to the naked eye. It will further be appreciated that a semi-transparent color layer permits a large percentages of photons to pass through (e.g., 80%) without being scattered or absorbed.

Figure 6:
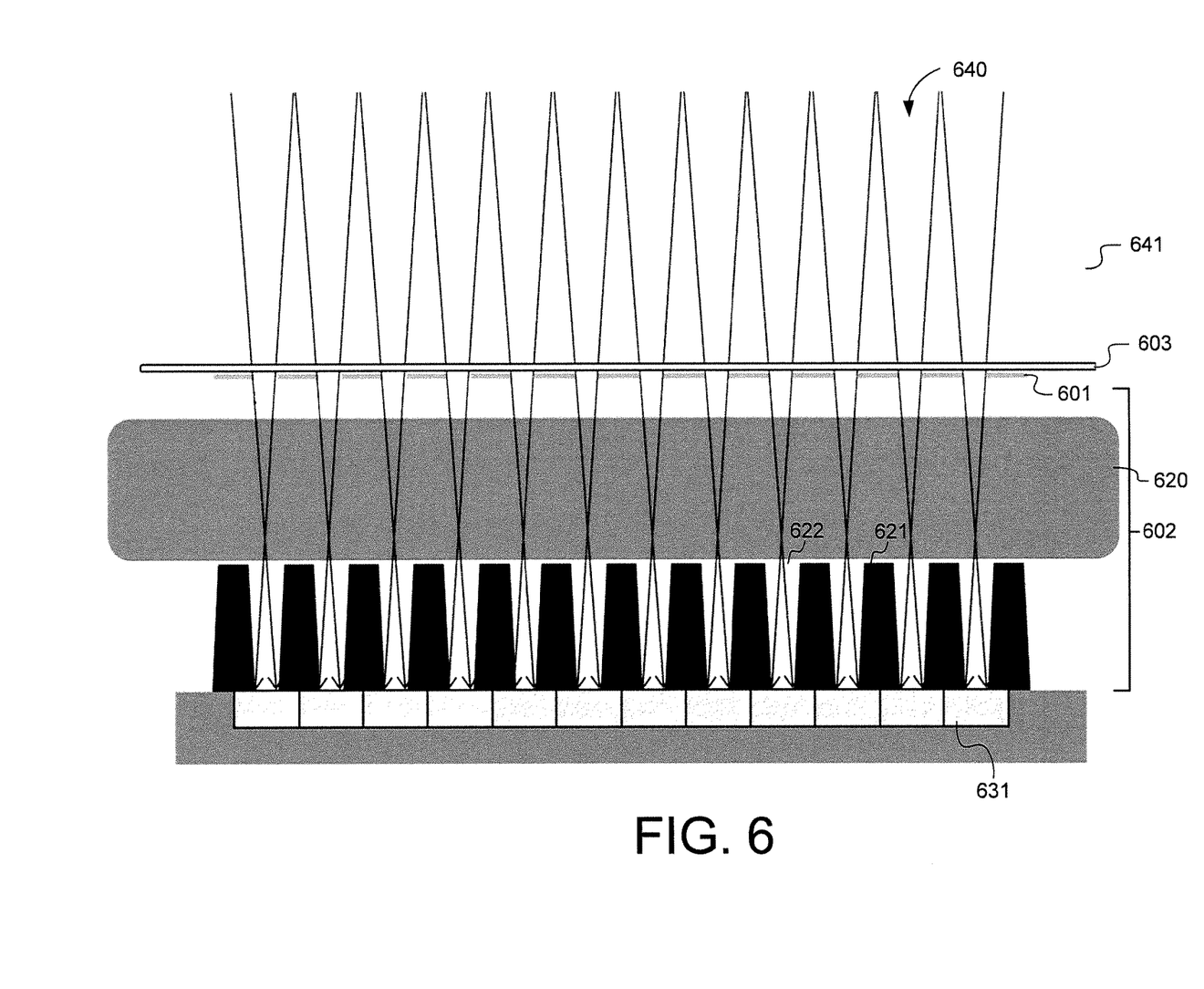
FIG. 6 is a block diagram of an example optical fingerprint sensor with an aperture layer and a collimating filter layer where the aperture layer is proximate to a semi-transparent color layer.

FIG. 6 is a block diagram of an example optical fingerprint sensor with an aperture layer 601 and a collimating filter layer 602 where the aperture layer is proximate to a semi-transparent color layer 603. The optical fingerprint sensor further includes a cover glass 641, the top of which provides an input surface 640. The semi-transparent color layer 603 may be coated on the underside of the cover glass 641 or formed on a separate film underneath the cover glass. The aperture layer 601 may be, for example, a reflective metal layer or an opaque color layer that reflects or absorbs light from the cover glass to provide a brighter or richer appearance for the color of the semi-transparent color layer 603, with apertures patterned in the reflective or opaque layer. If an opaque color layer is used for the aperture layer 601, it may have the same or a similar color to the semi-transparent color layer 603. The collimating filter layer 602 includes a transparent layer 620 (which in this example can also serve as an illumination layer or a light guide for a light source of the optical fingerprint sensor), and a plurality of light-blocking structures 621 forming a plurality of collimators with collimating areas 622. An image sensor having a plurality of light sensing elements 631 is also provided. The aperture layer 601 may be attached to the semi-transparent color layer 603 and/or the transparent layer 620, for example, using an adhesive. The operation of the compound collimating structure formed by the aperture layer 601 and collimating filter layer 602 is similar as discussed above with respect to the compound collimating structure depicted in FIGS. 4 and 5.

Figure 7:
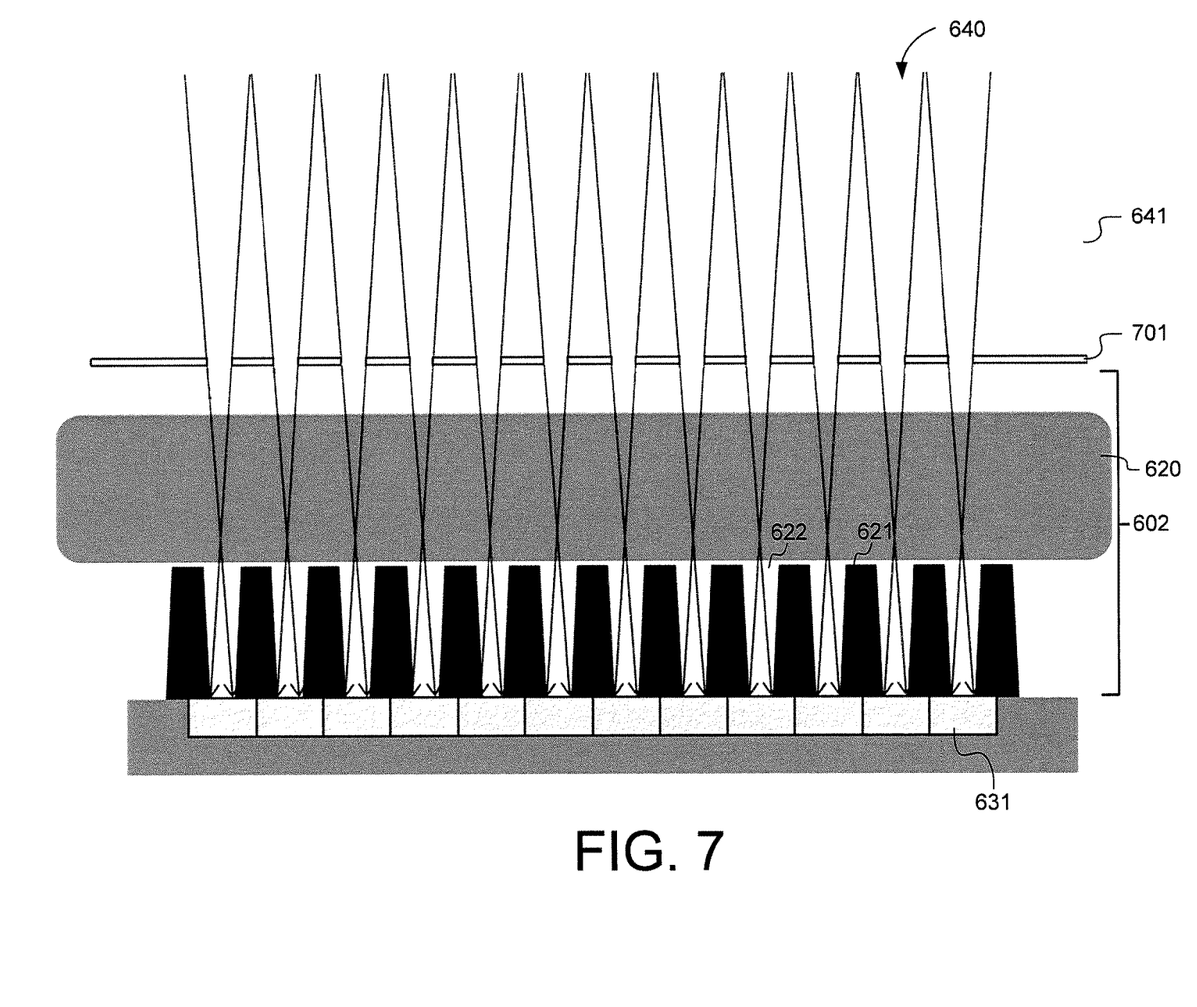
FIG. 7 is a block diagram of an example optical fingerprint sensor with an aperture layer and a collimating filter layer where the aperture layer is an opaque color layer with patterned apertures.

FIG. 7 is a block diagram of an example optical fingerprint sensor with an aperture layer 701 and a collimating filter layer 602 where the aperture layer 701 is a substantially opaque color layer with patterned apertures. It will be appreciated that the apertures, which may be for example 10 μm holes, can be substantially unnoticeable to the naked eye, allowing the aperture layer to not only act on the light reaching the detector but also double as a color layer for aesthetic affect. The optical fingerprint sensor further includes a cover glass 641, the top of which provides an input surface 640. The aperture layer 701 may be, for example, a patterned ink layer coated onto the cover glass 641 or formed on a film underneath the cover glass, which includes a plurality of apertures. The collimating filter layer 602 includes a transparent substrate 620 (which in this example can also serve as an illumination layer or light guide for a light source of the optical fingerprint sensor), and a plurality of light-blocking structures 621 forming a plurality of collimators with collimating areas 622. An image sensor having a plurality of light sensing elements 631 is also provided. The operation of the compound collimating structure formed by the aperture layer 601 and collimating filter layer 602 is similar as discussed above with respect to the compound collimating structure depicted in FIGS. 4 and 5.

In the exemplary configurations depicted in FIGS. 6 and 7, the illumination layer may be positioned beneath the aperture layer and/or color layer such that photons from the light source (not depicted), which may include, for example, LEDs or OLEDs, are both sent through the apertures on the way to the input object and reflected from the sensing region for the input object through the apertures on the way to the image sensor. In other exemplary embodiments, light from the light source may be provided directly to the input surface through the cover glass or directed into the cover glass in a total internal reflection (TIR) mode, such that light from the light source reaches the input surface through the cover glass and is reflected from the input object or input surface through the aperture layer and down to the image sensor.

It will be appreciated that, although the exemplary optical sensor having a compound collimating system depicted in FIGS. 6 and 7 have apertures in the aperture layer that are of a similar size to the size of the bottoms of the collimating areas, in other exemplary embodiments, the sizes of the apertures may be different from the size of the bottoms of the collimating areas. For example, the bottom of the collimating areas may have a 10-15 μm diameter while the patterned apertures have a diameter of 20-25 μm. The size and pitch of the apertures in a particular exemplary implementation may be based on the desired cosmetic appearance a device, as well as the desired performance of the optical sensor.

As shown in FIGS. 6 and 7, in certain exemplary implementations, the patterned apertures may be part of a metal layer (e.g., a reflective or dark metal layer as shown in FIG. 6), while in other exemplary implementations, the apertures may be in a patterned ink layer (e.g., a patterned ink layer under a cover glass as shown in FIG. 7). The apertures may be patterned, for example, via lithography, via a screen printing process, or other printing process.

In some exemplary embodiments, to the extent that the presence of the apertures in a metal layer or a patterned ink layer causes the appearance of the color in the metal layer or the ink layer to be different from the metal layer or the ink layer without apertures, the entire colored portion of a device may be provided with apertures in a metal layer or in a patterned ink layer to provide a consistent cosmetic appearance, if so desired.

In some exemplary embodiments where the patterned apertures are in a metal layer, the aperture layer may be used for other features as well, including finger presence detection to initiate fingerprint capture only when a finger is present over the sensor. In this case, the patterned metal aperture layer may double as one or more capacitive sensing electrodes that operates based on absolute or trans-capacitive sensing principles.

It will be appreciated that the use of the aperture layer in combination with the collimators in the compound collimating system discussed herein provides a small angle of acceptance for collection of photons by an image sensor such that a biometric object, even if it is hovering or partially hovering above the input surface (e.g., above the top of a cover glass), may be imaged without blurring or with minimal blurring.

It will be appreciated that although the examples discussed herein demonstrate the exemplary implementations of the disclosure with respect to fingerprint sensors, these techniques may also be used in other embodiments for other types of sensors having different resolutions beyond just sensors configured to detect fingerprint patterns.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An optical sensor system having a compound aperture and collimator structure for collimating light, comprising:
   an input surface providing a sensing region for a biometric object;
   an aperture layer comprising a plurality of apertures, disposed beneath the input surface;
   a plurality of light-blocking structures, separate from and disposed beneath the aperture layer, forming a plurality of collimators; and
   an image sensor, disposed beneath the plurality of light-blocking structures, wherein the image sensor is configured to detect light from the sensing region that has passed through the aperture layer and the plurality of collimators;
   wherein apertures of the aperture layer provide entrance apertures to the compound aperture and collimator structure; and
   wherein the plurality of light-blocking structures are configured to prevent cross-talk by blocking stray light from entering respective light sensing elements of the image sensor, wherein stray light relative to a respective light sensing element of the image sensor is light that is not transmitted through a respective aperture and collimator aligned with the respective light sensing element of the image sensor.

2. The optical sensor system according to claim 1, wherein collimators of the plurality of collimators are aligned to respective apertures of the aperture layer.

3. The optical sensor system according to claim 1, further comprising:
   a transparent layer, disposed between the aperture layer and the plurality of collimators.

4. The optical sensor system according to claim 3, wherein thickness of the transparent layer is 145 um or less.

5. The optical sensor system according to claim 1, wherein the plurality of light-blocking structures are formed of etched silicon.

6. The optical sensor system according to claim 1, wherein the plurality of light-blocking structures have heights of 105 um or less.

7. The optical sensor system according to claim 1, wherein the plurality of light-blocking structures have vertical walls.

8. The optical sensor system according to claim 1, wherein the plurality of light-blocking structures have slanted walls.

9. The optical sensor system according to claim 8, wherein an opening at a top of a collimator of the plurality of collimators formed by the plurality of light-blocking structures has a larger diameter than an aperture of the plurality of apertures in the aperture layer, and an opening at a bottom of a collimator of the plurality of collimators has a smaller diameter than the opening at the top of the collimator of the plurality of collimators.

10. The optical sensor system according to claim 1, wherein the aperture layer and the plurality of collimators are configured to provide, in combination, an aspect ratio of at least 15:1 for the light passing through the aperture layer and the plurality of collimators.

11. The optical sensor system according to claim 1, wherein thickness of the aperture layer is 100 nm or less.

12. The optical sensor system according to claim 1, further comprising:

an illumination layer, disposed beneath the aperture layer, configured to provide light to be reflected from the sensing region and detected by the image sensor.

13. The optical sensor system according to claim 1, wherein the aperture layer is formed of a light blocking metal.

14. The optical sensor system according to claim 1, further comprising:
a semi-transparent color layer, disposed above the aperture layer.

15. An optical sensor system having a compound aperture and collimator structure for collimating light, comprising:
an input surface providing a sensing region for a biometric object;
a color layer, comprising a plurality of apertures, disposed beneath the input surface;
a plurality of light-blocking structures, separate from and disposed beneath the color layer; and
an image sensor, disposed beneath the plurality of light-blocking structures, wherein the image sensor is configured to detect light from the sensing region that has passed through the color layer.

16. The optical sensor system according to claim 15, wherein the color layer further comprises:
a semi-transparent color layer; and
a reflective aperture layer comprising the plurality of apertures.

17. The optical sensor system according to claim 15, wherein the color layer further comprises:
a semi-transparent color layer; and
a dark aperture layer comprising the plurality of apertures.

18. The optical sensor system according to claim 15, wherein the color layer is an ink layer with the plurality of apertures formed in the ink layer.

19. A method for producing an optical biometric sensor having a compound aperture and collimator structure for collimating light, comprising:
forming a plurality of collimators over an image sensor, wherein the plurality of collimators are formed by a plurality of light blocking structures;
forming a transparent layer over the plurality of collimators; and
forming an aperture layer over the transparent layer, wherein the aperture layer comprises a plurality of apertures aligned to the plurality of collimators.

20. An optical sensor system having a compound aperture and collimator structure for collimating light, the optical sensor system comprising:
an aperture layer comprising a plurality of apertures;
a transparent layer, disposed beneath the aperture layer;
a plurality of light-blocking structures, disposed beneath the transparent layer, forming a plurality of collimators; and
an image sensor, disposed beneath the plurality of light-blocking structures, wherein the image sensor is configured to detect light from a sensing region for a biometric object above the aperture layer, wherein the detected light has passed from the sensing region through the aperture layer and the plurality of collimators.

* * * * *